US008907090B2

(12) United States Patent
Lohray et al.

(10) Patent No.: US 8,907,090 B2
(45) Date of Patent: Dec. 9, 2014

(54) PROCESSES FOR PREPARING DIFFERENT FORMS OF (S)-(+)-CLOPIDOGREL BISULFATE

(75) Inventors: Braj Bhushan Lohray, Gujarat (IN); Vidya Bhushan Lohray, Gujarat (IN); Bipin Pandey, Gujarat (IN); Mayank Ghanshyambhai Dave, Gujarat (IN); Parind Dholakia, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 2109 days.

(21) Appl. No.: 10/577,940

(22) PCT Filed: Nov. 2, 2004

(86) PCT No.: PCT/IN2004/000341
§ 371 (c)(1),
(2), (4) Date: Jul. 12, 2006

(87) PCT Pub. No.: WO2005/063708
PCT Pub. Date: Jul. 14, 2005

(65) Prior Publication Data
US 2007/0082924 A1    Apr. 12, 2007

(30) Foreign Application Priority Data

Nov. 3, 2003  (IN) .......................... 1154/MUM/2003
Nov. 25, 2003 (IN) .......................... 1217/MUM/2003

(51) Int. Cl.
*C07D 471/04*   (2006.01)
*C07D 495/04*   (2006.01)

(52) U.S. Cl.
CPC .................................. *C07D 495/04* (2013.01)
USPC ......................................... 546/114; 514/301

(58) Field of Classification Search
USPC ........................................ 514/301; 546/114
See application file for complete search history.

(56) References Cited

U.S. PATENT DOCUMENTS

| | | | |
|---|---|---|---|
| 4,847,265 A | 7/1989 | Badorc et al. | |
| 6,429,210 B1 | 8/2002 | Bousquet et al. | |
| 6,504,030 B1 | 1/2003 | Bousquet et al. | |
| 6,635,763 B2 * | 10/2003 | Pandey et al. | 546/114 |
| 6,767,913 B2 | 7/2004 | Lifshitz-Liron et al. | |
| 6,800,759 B2 * | 10/2004 | Valeriano et al. | 546/114 |
| 7,074,928 B2 | 7/2006 | Lifshitz-Liron et al. | |
| 7,291,735 B2 * | 11/2007 | Mukarram et al. | 546/114 |
| 7,446,200 B2 | 11/2008 | Deshpande et al. | |
| 7,470,707 B2 | 12/2008 | Yun et al. | |
| 7,714,133 B2 * | 5/2010 | Veverka et al. | 546/114 |
| 2002/0177712 A1 | 11/2002 | Pandey et al. | |
| 2002/0198229 A1 | 12/2002 | Bousquet et al. | |
| 2003/0114479 A1 | 6/2003 | Lifshitz-Liron et al. | |
| 2003/0225129 A1 | 12/2003 | Lifshitz-Liron et al. | |
| 2005/0203122 A1 | 9/2005 | Doser et al. | |
| 2005/0228012 A1 | 10/2005 | Yun et al. | |
| 2005/0256152 A1 | 11/2005 | Doser et al. | |
| 2006/0074242 A1 | 4/2006 | Deshpande et al. | |
| 2006/0154957 A1 | 7/2006 | Finkelstein et al. | |
| 2006/0264636 A1 | 11/2006 | Lohray et al. | |
| 2007/0037842 A1 | 2/2007 | Lohray et al. | |
| 2007/0082924 A1 | 4/2007 | Lohray | |
| 2008/0188663 A1 | 8/2008 | Kumar et al. | |
| 2008/0300409 A1 | 12/2008 | Finkelstein et al. | |
| 2008/0306268 A1 | 12/2008 | Finkelstein et al. | |

FOREIGN PATENT DOCUMENTS

| | | | |
|---|---|---|---|
| WO | 03/051362 A | | 6/2003 |
| WO | 2004/081016 A | | 9/2004 |
| WO | WO2005/012300 | * | 2/2005 |

OTHER PUBLICATIONS

Kirk-Othmer "crystallization" Encyclopedia of chem. tech. p. 95-147 (2002).*
Brittain "Using meltint point to . . . " p. 1-2 (2009).*
Mangum "The Gallium melting . . . " p. 723-724 (1977).*
Melting Point "Experiment" Oneonta.edu. p. 1-4 (2003).*
Murov "Properties of organic solvents" p. 1-7 (1998).*
"Solvent" Wikipdia, p. 1-10 (2001).*
2-hexanol, p. 1-2 , Wikipedia (2014).*
1-pentanol, p. 1-2, Wikipedia (2014).*
Gattermann "Laboratory method . . . " p. 4-5 (1937).*
Lohray et al. "Process for prepartion of . . . " CA143:139168 (2005).*
International Search Report of PCT/IN2004/000341, Aug. 5, 2005.
Byrn et al. *Solid-State Chemistry of Drugs*, Academic Press, pp. 3-9 (1982).
Byrn et al. "Solid-state pharmaceutical chemistry" *Chem. Mater.*, vol. 6, No. 8, pp. 1148-1158 (1994).
Dunitz et al. "Disappearing polymorphs" *Acc. Chem. Res.*, vol. 28, No. 4, pp. 193-200 (1995).
Guillory "Generation of polymorphs, hydrates, solvates, and amorphous solids" in *Polymorphism in Pharmaceutical Solids (Drugs & Pharmaceutical Sciences Series)* (Brittain ed.), vol. 95, pp. 208-219 (1999).
Hancock & Zografi "Characteristics and significance of the amorphous state in pharmaceutical systems" *J. Pharm. Sci.*, vol. 86, No. 1, pp. 1-12 (1997).
Knapman "Polymorphic prediction" *Modern Drug Discovery*, vol. 3, No. 2, pp. 53-54 and 57, four sheets (2000).
Int'l Preliminary Report on Patentability for PCT/IN2004/000341, 14 pages (Dec. 2005).

* cited by examiner

*Primary Examiner* — Celia Chang
(74) *Attorney, Agent, or Firm* — Nixon & Vanderhye P.C.

(57) ABSTRACT

The invention provides improved processes for the preparation of hydrated form of (S)-(+)-Clopidogrel bisulfate as well as improved processes for the preparation of form-I and form-II of (S)-(+)-Clopidogrel bisulfate.

14 Claims, No Drawings

PROCESSES FOR PREPARING DIFFERENT FORMS OF (S)-(+)-CLOPIDOGREL BISULFATE

This application is the US national phase of international application PCT/IN2004/000341, filed 2 Nov. 2004, which designated the U.S. and claims priority of IN 1154/MUM/2003, filed 3 Nov. 2003, and IN 1217/MUM/2003, filed 25 Nov. 2003, the entire contents of each of which are hereby incorporated by reference.

FIELD OF INVENTION

The present invention relates to improved processes for the preparation of different forms of clopidogrel bisulfate. The present invention particularly describes improved processes for the preparation of amorphous (S)-(+)-Clopidogrel bisulfate and Form I of (S)-(+)-Clopidogrel bisulfate. More particularly, in a preferred embodiment, the present invention discloses improved processes for the preparation of amorphous form of (S)-(+)-Clopidogrel bisulfate as hydrates, solvates and various pharmaceutical compositions containing the amorphous forms prepared according to the present invention.

In another preferred embodiment, this invention describes improved processes for the preparation of Form I, Form II polymorphs of S-(+)-Clopidogrel bisulfate and pharmaceutical compositions containing them. (S)-(+)-Clopidogrel bisulfate an antiplatelet drug is currently being marketed for the treatment of atherosclerosis, myocardial infraction, strokes and vascular death. The present invention also describes a method of treatment of such cardiovascular disorders using the different forms of Clopidogrel bisulfate or mixtures thereof prepared according to the present invention, and pharmaceutical compositions containing them. The present invention further relates to the use of the different forms of (S)-(+)-Clopidogrel bisulfate prepared according to the processes disclosed herein and pharmaceutical compositions containing them for the treatment of cardiovascular disorders.

BACKGROUND OF THE INVENTION

Clopidogrel bisulfate corresponds to the empirical formula $C_{16}H_{16}ClNO_2S.H_2SO_4$. Chemically it is methyl (+)-(S)-alpha-(2-chlorophenyl)-6,7-dihydrothieno[3,2-c]pyridine-5 (4H)-acetate sulfate (1:1), having the following structural formula.

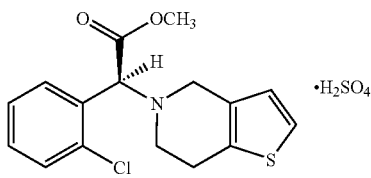

Clopidogrel is an inhibitor of platelet aggregation and is marketed as an antianginal agent, antiplatelet agent and is found to decrease morbid events in people with established atherosclerotic cardiovascular disease and cerebrovascular diseases.

The therapeutic application of Clopidogrel as blood-platelet aggregation inhibiting agents and antithrombotic agent and its preparation is disclosed in U.S. Pat. No. 4,529,596.

U.S. Pat. No. 4,847,265 describes the process for the preparation of the hydrogen sulfate salt of Clopidogrel.

Various other strategies to prepare Clopidogrel are disclosed in WO 98/51681, WO 98/51682, WO 98/51689, WO 99/18110, U.S. Pat. No. 5,036,156, U.S. Pat. No. 5,132,435, U.S. Pat. No. 5,139,170, U.S. Pat. No. 5,204,469 and U.S. Pat. No. 6,080,875.

U.S. Pat. No. 4,847,265 discloses that the dextrorotatory enantiomer of formula (I) of Clopidogrel has an excellent antiaggregant platelet activity, whereas the corresponding levorotatory enantiomer is less tolerated and is less active. U.S. Pat. No. 4,847,265 relates to the dextrorotatory enantiomer and its pharmaceutically acceptable salts with platelet aggregation inhibiting activity.

Subsequently filed Patent Application WO 99/65915 (U.S. Pat. No. 6,429,210) titled "Polymorphic Clopidogrel hydrogen sulfate form", which is herein incorporated by reference, discloses the existence of a specific polymorphic Form II of the hydrogen sulfate of (S)-(+)-Clopidogrel (m.p.=176±3° C.). It is also disclosed in this patent application that the earlier processes described in the U.S. Pat. No. 4,847,265 gives Form I (m.p. 184±3° C.). These two crystalline polymorphic forms I and II differed in their stability, physical properties, spectral characteristics and their method of preparation. However, both the polymorphs have similar bioavailability, as shown in their bioequivalence in healthy human volunteers.

Although, U.S. Pat. No. 4,847,265 reports the formation of (S)-(+)-Clopidogrel bisulfate salt with m.p. 184° C., it was disclosed as Form I only in patent application WO 99/65915. However, a reproducible and consistent method for the preparation of Form I with chirally pure material (ee>99%) was in doubt since chiral purity of the material (Clopidogrel bisulfate) with m.p. 184±3° C., disclosed in U.S. Pat. No. 4,847,265 was not precisely known.

In fact, we have observed that formation of Form I of (S)-(+)-Clopidogrel bisulfate with chiral purity>99% e.e. is inconsistent and difficult to reproduce using the procedures reported in U.S. Pat. No. 4,847,265 and WO 99/65915 whereas the formation of Form II is extremely facile and consistent with optically pure (S)-(+)-Clopidogrel free base.

We have earlier disclosed improved processes for the manufacture of (S)-(+)-Clopidogrel bisulfate & its intermediates [Indian Patent Applications 84/MUM/2001 (WO 02059128/U.S. Pat. No. 6,635,763), & 335/MUM/2001] which are cited herein in their entirety as reference.

We have also disclosed hydrated form of amorphous Clopidogrel bisulfate as well as methanolates, ethanolates and containing different form stabilizers [Indian patent application 1154/MUM/2003 and 413/MUM/2003], which are also incorporated as reference.

Amorphous Clopidogrel bisulfate and other solvated forms (1-butanol, 2-butanol, isopropanol, 1-propanol) as well mixtures of amorphous form with Form I and Form II and processes for preparing them have been disclosed in Teva's application no. WO 03/051362 A2, which is cited herein as reference. However, this application does not disclose amorphous Clopidogrel bisulfate hydrate.

Teva's application also discloses processes for preparing Form I and Form II of Clopidogrel bisulfate. The Form I is prepared by contacting the amorphous form disclosed therein in ethers preferably diethyl ether or MTBE. These processes have the following disadvantages:
i. diethyl ether and MTBE are very volatile and inflammable hence are hazardous to work with;
ii. the process is difficult to be scaled up to plant scale;
iii. problem of recovery of antisolvents further making the process economically unfeasible.

We herein disclose improved processes for preparing amorphous Clopidogrel bisulfate, amorphous Clopidogrel bisulfate hydrate, amorphous Clopidogrel bisulfate solvates, with high optical purity (ee>99%).

We also disclose improved processes for preparing Form I and Form II of Clopidogrel bisulfate. Also disclosed are amorphous Clopidogrel bisulfate, Form I and Form II of Clopidogrel bisulfate with characteristic impurity profile.

OBJECTS OF THE INVENTION

It is an object of the present invention to provide an improved processes for preparation of amorphous (S)-(+)-Clopidogrel bisulfate in hydrate form containing from about 1-4% water.

Yet another object of the present invention is to provide improved processes for the preparation of amorphous Clopidogrel bisulfate solvates.

A still further object of the present invention is to provide improved processes for the preparation of Form I of Clopidogrel bisulfate.

A still further object of the present invention is to provide improved processes for the preparation of Form II of Clopidogrel bisulfate.

As an embodiment of the present invention pharmaceutical compositions containing the various amorphous forms of Clopidogrel bisulfate, Form I and Form II described herein and prepared according to the present invention are provided.

Also is provided a method of treatment and use of the various amorphous forms of Clopidogrel bisulfate, Form I and Form II described herein and prepared according to the present invention for the treatment of cardiovascular disorders, comprising administering, for example, orally a composition of the invention in a therapeutically effective amount.

These processes are easy to scale up, commercially viable, safe, easy to handle and provides operational simplicity.

DESCRIPTION OF INVENTION

The present invention discloses improved processes for the preparation of different forms of clopidogrel bisulfate.

The present invention provides improved processes for the preparation of different amorphous forms of Clopidogrel bisulfate as described else where in the specification. The term "amorphous", as used herein, relates to solid material which lacks a regular crystalline structure. In a powder X-ray diffractogram such material gives no good intensity peaks. Whenever sulfuric acid is being used for preparing the bisulfate salt as disclosed in the specification, it is used in the range of 0.95-1.25 mole equivalent. The term Clopidogrel base, Clopidogrel bisulfate used in the specification means (S)-(+)-Clopidogrel base and (S)-(+)-Clopidogrel bisulfate respectively.

The various amorphous forms (hydrates, solvates, amorphous form containing form stabilizers) described in the specification can be prepared by any of the processes described below or used in combination.

i) clopidogrel base in suitable solvents is treated with dil. $H_2SO_4$, the solvent is evaporated and amorphous form is precipitated by addition of a suitable antisolvent(s). Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and the like or mixtures thereof. Suitable antisolvents may be selected from pentane, n-hexane, heptane, cyclohexane, pet ethers and the like or mixtures thereof ii) clopidogrel base in suitable solvents and water is treated with concentrated $H_2SO_4$, the solvent is evaporated and amorphous form is precipitated by addition of a suitable antisolvent(s). Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and the like or mixtures thereof. Suitable antisolvents may be selected from pentane, n-hexane, heptane, cyclohexane, pet ethers and the like or mixtures thereof iii) clopidogrel bisulfate in dichloromethane-water is treated with suitable bases, to obtain Clopidogrel base which is then treated with dil. $H_2SO_4$ in suitable solvents, the solvent is evaporated and the amorphous form is precipitated by addition of a suitable antisolvent(s). Suitable bases can be selected from NaOH, KOH, LiOH, $NaHCO_3$, $Na_2CO_3$, $K_2CO_3$ and the like. Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and the like or mixtures thereof. Suitable antisolvents may be selected pentane, n-hexane, heptane, cyclohexane, pet ethers and the like or mixtures thereof iv) clopidogrel bisulfate in dichloromethane—water is treated with suitable bases, to obtain Clopidogrel base which is then treated with concentrated $H_2SO_4$ in a mixture of suitable solvents and water, the solvent is evaporated and amorphous form precipitated by addition of suitable antisolvent(s). Suitable bases can be selected from NaOH, KOH, LiOH, $NaHCO_3$, $Na_2CO_3$, $K_2CO_3$, organic bases like tertiary alkyl amines and the like. Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and the like or mixtures thereof. Suitable antisolvents may be selected pentane, n-hexane, heptane, cyclohexane, pet ethers and the like or mixtures thereof v) (S)-(+) Clopidogrel camphor-sulfonate in suitable solvents like ethyl acetate, dichloromethane, dichloroethane, chloroform and the like and water is treated with a suitable base, to obtain Clopidogrel base which is then treated with dil. $H_2SO_4$ in suitable solvents. The solvent is evaporated and amorphous form is precipitated by addition of suitable antisolvent(s). Suitable bases can be selected from NaOH, KOH, LiOH, $NaHCO_3$, $Na_2CO_3$, $K_2CO_3$, organic bases like tertiary alkyl amines and the like. Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and the like or mixtures thereof. Suitable antisolvents may be selected from pentane, n-hexane, heptane, cyclohexane, pet ethers and the like or mixtures thereof vi) (S)-(+) Clopidogrel camphor-sulfonate in suitable solvents like ethyl acetate, dichloromethane, dichloroethane, chloroform and the like and water is treated with a suitable base, to obtain Clopidogrel base which is then treated with concentrated $H_2SO_4$ in a mixture of suitable solvent(s) and water. The solvent is evaporated and amorphous form precipitated by addition of suitable antisolvent. Suitable bases can be selected from NaOH, KOH, LiOH, $NaHCO_3$, $Na_2CO_3$, $K_2CO_3$, organic bases like tertiary alkyl amines and the like. Suitable solvents can be selected from methanol, ethanol, propanol, isopropanol, 1-butanol, 2-butanol, dichloromethane, dimethyl formamide, dimethyl acetamide, 1,4-dioxane, tetrahydrofuran and mixtures thereof. Suitable antisolvents may be selected from pentane, 2-hexane, heptane, cyclohexane, pet ethers and the like or mixtures thereof.

Various polyethylene glycols (PEG) 200, 400, 800, 900, 1000, 1200, 2000 and 4000 can also be used as amorphous form stabilizers in any of the processes described above.

Alternatively, the processes [(i)-(vi)] described above can be repeated by using the Clopidogrel base, (S)-(+) Clopidogrel bisulfate and (S)-(+) Clopidogrel camphor-sulfonate prepared according to the improved processes described by the applicant in WO 02059128/U.S. Pat. No. 6,635,763.

The present invention also describes improved processes for the preparation of Form I of Clopidogrel bisulfate from the different amorphous forms prepared according to any of the processes of the present invention. The Form I is obtained by treating the above amorphous forms in a mixture of diethyl ether-heptane, diethyl ether-hexane, diethyl ether-pet ethers in various combination and proportion, with a view to enhance operational safety, scalability and simplicity.

The Form I can also be prepared by any of the processes described below either alone or used in combination:

(i) clopidogrel base in suitable solvent(s) selected from $C_6$-$C_{12}$ alcohols is treated with dil. $H_2SO_4$, to obtain Form I of (S)-(+)-Clopidogrel bisulfate. Suitable solvents can be selected from $C_6$-$C_{12}$ alcohols which may be linear or branched, primary, secondary or tertiary alcohols such as 1-hexanol, 2-hexanol, 3-hexanol, isohexanol, 1-heptanol, 2-heptanol, 3-heptanol, 4-heptanol, octanol, isooctanol, decanol, and the like or mixtures thereof.

(ii) clopidogrel base in suitable solvent(s) selected from $C_6$-$C_{12}$ alcohols and a trace of water is treated with concentrated $H_2SO_4$, to obtain Form I of (S)-(+)-Clopidogrel bisulfate. Suitable solvents may be selected from $C_6$-$C_{12}$ alcohols which may be linear or branched, primary, secondary or tertiary alcohols such as hexanol, 2-hexanol, 3-hexanol, isohexanol, 1-heptanol, 2-heptanol, 3-heptanol, 4-heptanol, octanol, isooctanol, decanol, and the like or mixtures thereof.

(iii) clopidogrel bisulfate in any form including different crystalline forms such as Forms II, III, IV, V, VI etc. or amorphous form or in the form of oil is dissolved/contacted with suitable solvent(s) selected from $C_6$-$C_{12}$ alcohols to obtain Form I of (S)-(+)-Clopidogrel bisulfate. Suitable solvents can be selected from $C_6$-$C_{12}$ alcohols which may be linear or branched, primary, secondary or tertiary alcohols such as 1-hexanol, 2-hexanol, 3-hexanol, isohexanol, 1-heptanol, 2-heptanol, 3-heptanol, 4-heptanol, octanol, isooctanol, decanol, and the like or mixtures thereof.

(iv) clopidogrel bisulfate in any form including crystalline forms II, III, IV, V, VI etc. or amorphous form or in the form of oil is dissolved/contacted with suitable solvent(s) selected from $C_6$-$C_{12}$ alcohols and a trace of water, to obtain Form I of (S)-(+)-Clopidogrel bisulfate. Suitable solvent(s) can be selected from $C_6$-$C_{12}$ alcohols which may be linear or branched, primary, secondary or tertiary alcohols such as 1-hexanol, 2-hexanol, 3-hexanol, isohexanol, 1-heptanol, 2-heptanol, 3-heptanol, 4-heptanol, octanol, isooctanol, decanol, and the like or mixtures thereof.

(v) (S)-(+) Clopidogrel camphor-sulfonate in suitable solvent(s) like ethyl acetate, dichloromethane, dichloroethane, chloroform and the like and water is treated with suitable base(s), to obtain Clopidogrel base which is then treated with dil. $H_2SO_4$ in suitable solvent(s), selected from $C_6$-$C_{12}$ alcohols to obtain Form I of (S)-(+)-Clopidogrel bisulfate. Suitable bases can be selected from NaOH, KOH, LiOH, NaHCO$_3$, Na$_2$CO$_3$, K$_2$CO$_3$, organic bases like tertiary alkyl amines and the like. Suitable solvents can be selected from $C_6$-$C_{12}$ alcohols which may be linear or branched, primary, secondary or tertiary alcohols such as 1-hexanol, 2-hexanol, 3-hexanol, isohexanol, 1-heptanol, 2-heptanol, 3-heptanol, 4-heptanol, octanol, isooctanol, decanol, and the like or mixtures thereof.

(vi) clopidogrel camphor-sulfonate in suitable solvent(s) like ethyl acetate, dichloromethane, dichloroethane, chloroform and the like and water is treated with suitable base(s), to obtain Clopidogrel base which is then treated with concentrated $H_2SO_4$ in suitable solvent(s), selected from $C_6$-$C_{12}$ alcohols and a trace of water to obtain Form I of (S)-(+)-Clopidogrel bisulfate. Suitable bases can be selected from NaOH, KOH, LiOH, NaHCO$_3$, Na$_2$CO$_3$, K$_2$CO$_3$, organic bases like tertiary alkyl amines and the like. Suitable solvents can be selected from $C_6$-$C_{12}$ alcohols which may be linear or branched, primary, secondary or tertiary alcohols such 1-hexanol, 2-hexanol, 3-hexanol, isohexanol, 1-heptanol, 2-heptanol, 3-heptanol, 4-heptanol, octanol, isooctanol, decanol, and the like or mixtures thereof.

Alternatively, the processes [(i)-(vi)] described above can be repeated by using the Clopidogrel base, Clopidogrel bisulfate and (S)-(+) Clopidogrel camphor-sulfonate prepared according to the improved processes described by the applicant in U.S. Pat. No. 6,635,763.

The present invention also describes improved process for the preparation of Form II of Clopidogrel bisulfate from the different amorphous forms prepared according to any of the processes of the present invention. Form II is obtained by stirring the different amorphous forms in solvents like, MTBE and the like or their mixtures.

The amorphous forms of (S)-(+)-Clopidogrel bisulfate including hydrates/solvates (methanolates, ethanolates and the like), Form I and Form II of (S)-(+)-Clopidogrel bisulfate prepared according to the processes of the present invention may be characterized by their melting point, physical characteristics, X-ray powder diffraction pattern, DSC, thermogravimetric analysis, differential scanning calorimetry, diffused reflection IR absorption and/or by its solid state nuclear magnetic resonance spectrum and % content of water, methanol, ethanol and other solvates mentioned in processes described elsewhere in the specification, including form stabilizers like various PEGs.

The advantages of the processes for preparation of different forms of clopidogrel bisulfate according to the present not hazardous as it does not use volatile chemicals like ethers.

scalable at plant level and so industrially useful easy to operate good recovery of solvents gives high yield The different forms of amorphous (S)-(+)-Clopidogrel bisulfate hydrates/solvates (methanolates, ethanolates and the like), Form I and Form II of (S)-(+)-Clopidogrel bisulfate prepared according to the processes of the present invention may be administered orally, parenterally or rectally without further formulation, or any pharmaceutically acceptable liquid carrier. The drug substance of the present invention may also be filled in a capsule directly for oral administration. However, it is preferred that the drug substance is formulated with one or more excipients to prepare a pharmaceutical composition, for example, an oral dosage form.

Another aspect of the present invention aims at providing the various pharmaceutical compositions of the different amorphous forms of (S)-(+)-Clopidogrel bisulfate, Form I and Form II of (S)-(+)-Clopidogrel bisulfate prepared according to the present invention.

According to the present invention, the various amorphous forms of (S)-(+)-Clopidogrel bisulfate, Form I and Form II prepared according to the processes of the present invention is formulated into pharmaceutical compositions for oral use containing required amount of the active ingredient per unit of dosage, in combination with at least one pharmaceutical excipient in the form of tablets, sugar coated tablets, capsules, injectable solutions, granules or a syrup. They can also be administered rectally in the form of suppositories or can be parentally administered in the form of an injectable solution.

In another embodiment of the present invention a method of treatment and use of the different amorphous forms of (S)-(+)-Clopidogrel bisulfate, Form I and Form II prepared according to the present invention, for the treatment of cardiovascular disorders is provided, comprising administering, for example, orally or in any other suitable dosage forms, a composition of the invention in a therapeutically effective amount.

The following non-limiting examples illustrate the inventor's preferred methods for preparing the amorphous forms as well as Form I & Form II of (S)-(+)-Clopidogrel bisulfate discussed in the invention and should not be construed as limiting the scope of the invention in any way.

EXAMPLE 1

Preparation of Clopidogrel Hydrogen Sulfate Hydrated Amorphous Form

Clopidogrel base (444.18 gms) was dissolved in methanol (4.136 L) with stirring at 25 to 30° C. Dilute sulfuric acid was added to the solution dropwise in about 15 minutes of time at 5 to 10° C. The reaction mixture was stirred for 30 minutes. Then the solvent was evaporated under reduced pressure at 50 to 55° C. Cyclohexane (2 L) was added to reaction mixture and the same was stirred, filtered and dried at 45 to 50° C. in a vacuum oven for 8 hours to obtain powder (493 gms, 85%) whose characterization data showed to be the hydrated amorphous form. KF value is found in the range from 1 to 3% water (in different batches) and powder XRD data indicated to be amorphous with no peaks due to crystalline form.

EXAMPLE 2

Preparation of Clopidogrel Hydrogen Sulfate Hydrated Amorphous Form

Clopidogrel base (500 gms) was dissolved in methanol (4.65 L) and water (65 ml) with stirring at 25 to 30° C. Concentrated sulfuric acid was added to the solution dropwise in about 15 minutes of time at 5 to 10° C. The reaction mixture was stirred for 30 minutes. Then the solvent was evaporated under reduced pressure at 50 to 55° C. Cyclohexane (2 L) was added to the reaction mixture. The reaction mixture was stirred, filtered and dried at 45 to 50° C. in a vacuum oven for 8 hours to obtain powder (600 gms, 92%) whose characterization data showed to be the hydrated amorphous form. KF value is found in the range from 1 to 3% (in different batches) and powder XRD data indicated to be amorphous with no peaks due to crystalline form.

EXAMPLE 3

Preparation of Clopidogrel Hydrogen Sulfate Hydrated Amorphous Form

Suspension of Clopidogrel hydrogen sulfate (50 gms) was stirred in dichloromethane (300 ml) and subsequently basified by adding NaHCO$_3$ solution (10%, 500 ml) in it. The mixture was stirred at 25 to 30° C. for about 10 minutes. The layers were separated and the aqueous layer was extracted with dichloromethane (50 ml.) and washed with water (100 ml.). It was then dried over Na$_2$SO$_4$ and the solvent was distilled off on a water bath at 50 to 55° C. to obtain Clopidogrel free base (39.5 gms).

The Clopidogrel base (38.3 gms) obtained above was dissolved in methanol (356 mL) and water (5 ml) at 25 to 30° C. Concentrated sulfuric acid was added to the solution dropwise in about 15 minutes of time at 5 to 10° C. The reaction mixture was stirred for 30 minutes. The solvent was evaporated under reduced pressure at 50 to 55° C. Cyclohexane (175 mL) was added to the reaction mixture and stirred for approximately 10 minutes and filtered, dried at temperature in the range from 45 to 50° C. in a vacuum oven for approximately 8 hours to obtain powder (46 gms, 92%) whose characterization data showed to be the hydrated amorphous form. KF value is found in the range from 1 to 3% (in different batches) and powder XRD data indicated to be amorphous with no peaks due to crystalline form.

EXAMPLE 4

Preparation of Clopidogrel Hydrogen Sulfate Hydrated Amorphous Form

Suspension of Clopidogrel hydrogen sulfate (61 gms) was stirred in dichloromethane (360 ml) and subsequently basified with NaHCO$_3$ solution (10%, 600 ml). The mixture was stirred at 25 to 30° C. for about 10 minutes. The layers were separated and the aqueous layer was extracted with dichloromethane (60 ml.) and washed with water (120 ml.). It was then dried over Na$_2$SO$_4$ and the solvent was distilled off on a water bath at a temperature in the range from 50 to 55° C. to obtain Clopidogrel free base (46.0 gms)

Clopidogrel base (46 gms) obtained above was dissolved in methanol (427 mL) at 25 to 30° C. Dilute sulfuric acid was added to the solution dropwise in about 15 minutes at 5 to 10° C. The reaction mixture was stirred for 30 minutes. The solvent was evaporated under reduced pressure at 50 to 55° C. Cyclohexane (190 mL) was added to the reaction mixture and stirred for approximately 10 minutes and filtered, and dried at temperature in the range from 45 to 50° C. in a vacuum oven for approximately 8 hours to obtain powder (54 gms, 90%) whose characterization data showed to be the hydrated amorphous form. KF value is found in the range from 1 to 3% (in different batches) and powder XRD data indicated to be amorphous with no peaks due to crystalline form.

EXAMPLE 5

Preparation of Clopidogrel Hydrogen Sulfate Hydrated Amorphous Form

A suspension of (S)-(+) Clopidogrel camphor sulphonate (66 gms) was stirred in dichloromethane (300 ml) and subsequently basified with NaHCO$_3$ solution (10%, 500 ml). The mixture was stirred at 25 to 30° C. for about 10 minutes. The layers were separated and the aqueous layer was extracted with dichloromethane (50 ml.) and washed with water (100 ml.). It was then dried over $Na_2SO_4$ and the solvent was distilled off on a water bath at a temperature in the range from 50 to 55° C. to obtain Clopidogrel free base (39.5 gms)

Clopidogrel base (38.3 gms) obtained above was dissolved in methanol (356 mL) at 25 to 30° C. Dilute sulfuric acid was added to the solution dropwise in about 15 minutes of time at 5 to 10° C. The reaction mixture was stirred for 30 minutes. Then the solvent was evaporated under reduced pressure at 50 to 55° C. Cyclohexane (175 mL) was added to the reaction mixture and stirred for approximately 10 minutes and filtered, dried at 45 to 50° C. in a vacuum oven for approximately 8 hours to obtain powder (46 gms, 92%) whose characterization data showed to be the hydrated amorphous form. KF value is found in the range from 1 to 3% (in different batches) and powder XRD data indicated to be amorphous with no peaks due to crystalline form.

EXAMPLE 6

Preparation of Clopidogrel Hydrogen Sulfate Hydrated Amorphous Form

A suspension of (S)-(+) Clopidogrel camphor sulphonate (132 gms) was stirred in dichloromethane (600 ml) and subsequently basified with $NaHCO_3$ solution (10%, 1000 ml). The mixture was stirred at a temperature in the range from 25 to 30° C. for about 10 minutes. The layers were separated and aqueous layer was extracted with dichloromethane (100 ml.) and washed with water (200 ml.). The organic layer was then dried over $Na_2SO_4$ and solvent was distilled off on a water bath at a temperature in the range from 50 to 55° C. to obtain Clopidogrel free base (79 gms)

Clopidogrel base (76.6 gms) obtained above was dissolved in methanol (712 mL) and water (10 ml) at 25 to 30° C. Concentrated sulfuric acid was added to the solution dropwise in about 15 minutes of time at 5 to 10° C. The reaction mixture was stirred for 30 minutes. The solvent was evaporated under reduced pressure at 50 to 55° C. Cyclohexane (350 mL) was added to the reaction mixture and stirred for approximately 10 minutes, filtered and dried at 45 to 50° C. in a vacuum oven for approximately 8 hours to obtain powder (90 gms, 90%) whose characterization data showed to be the hydrated amorphous form. KF value is found in the range from 1 to 3% (in different batches) and powder XRD data indicated to be amorphous with no peaks due to crystalline form.

EXAMPLE 7

Preparation of Clopidogrel Hydrogen Sulfate Hydrated Amorphous Form

A suspension of (S)-(+) Clopidogrel hydrogen sulfate (110 gms) was stirred in dichloromethane (1.1 L) The solution was stirred at 25 to 30° C. Water (132 ml) was added and the reaction mixture was stirred for approximately 10 minutes. The reaction mixture was distilled at atmospheric pressure, on a water bath at a temperature in the range from 50 to 55° C. and high vacuum was applied. Dichloromethane (500 ml) was again added to it, excess solvent was distilled off applying high vacuum at 50 to 55° C. The operation was repeated with 500 ml dichloromethane. Finally 250 ml dichloromethane was charged to the mixture and subsequently the solvent was distilled off using high vacuum at a temperature 50 to 55° C., and a solid was obtained as a free flowing solid. It was scratched and vacuum was reapplied for 10 to 15 minutes. Solid was transferred in to a drier in a dry area, dried at 50-53° C. for 8 hrs. to obtain powder (100 gms) whose characterization data showed to be the hydrated amorphous form.

EXAMPLE 8

Preparation of Clopidogrel Hydrogen Sulfate Form I

Clopidogrel base (925 gms) was dissolved in n-hexanol (4.6 L) with stirring at 25 to 30° C. Dilute sulfuric acid was added to the reaction mixture at 10 to 15° C. The mixture was seeded with form-I crystal at 20 to 25° C. The reaction mixture was stirred for approximately 8 to 10 hours & subsequently further stirred for 8-10 hrs at 22 to 25° C. with low agitation. The solid was then filtered and washed with methyl tert butyl ether (1875 ml) and subsequently dried at 30 to 35° C. on a drier, to get 1095 g of clopidogrel bisulfate salt as crystals. Subsequent analysis confirmed that the crystals were clopidogrel hydrogen sulfate Form-I.

EXAMPLE 9

Preparation of Clopidogrel Hydrogen Sulfate Form I

Clopidogrel base (500 gms) was dissolved in n-hexanol (2.5 L) with stirring at 25 to 30° C. and water (10.3 ml) was added to it. Concentrated $H_2SO_4$ was added at 10-15° C. The reaction mixture was seeded with form-I crystal at 20-25° C. The mixture was stirred at room temperature for 10-12 hrs and subsequently it was stirred at 22 to 25° C., for 1-2 hours with high agitation. The mixture was further stirred for 5-8 hours at room temperature with low agitation. It was filtered, washed with methyl tert butyl ether (1500 ml) and dried at a temperature in the range from 30 to 35° C. in a drier, to get 525 g of salt as crystals. Subsequent analysis confirmed that the crystals were clopidogrel hydrogen sulfate Form-I.

EXAMPLE 10

Preparation of Clopidogrel Hydrogen Sulfate Form I

Suspension of Clopidogrel hydrogen sulfate (660 gms) was stirred in dichloromethane (3900 ml) & subsequently basified with $NaHCO_3$ solution (10%, 6500 ml). The reaction mixture was stirred at 25 to 30° C. for about 10 minutes. The layers were separated and the aqueous layer was extracted with dichloromethane (650 ml.) and washed with water (1300 ml.). It was then dried over $Na_2SO_4$ and the solvent was distilled off on a water bath at 50 to 55° C. to obtain Clopidogrel free base (505 gms).

Clopidogrel base (500 gms) obtained above was dissolved in n-hexanol (2.5 L) with stirring at 25 to 30° C. and water (10.3 ml) was added to it. Concentrated sulfuric acid was added at 10 to 15° C. The reaction mixture was seeded with form-I crystals at a temperature in the range from 20 to 25° C. The mixture was stirred at 25 to 30° C. for 10-12 hrs & subsequently it was stirred at high agitation, at a temperature in the range from 22 to 25° C. for 1-2 hrs. The reaction mixture was further stirred for 5-8 hrs at 22 to 25° C., at low agitation. The mixture was then filtered, washed with methyl tert butyl ether (1500 ml) and dried at 30-35° C. in a drier, to obtain 561 g clopidogrel bisulfate salt. Subsequent analysis confirmed that the crystals were clopidogrel hydrogen sulfate Form-I.

EXAMPLE 11

Preparation of Clopidogrel Hydrogen Sulfate Form I

A suspension of Clopidogrel hydrogen sulfate (330 gms) was stirred in dichloromethane (1950 ml) and subsequently with NaHCO$_3$ solution (10%, 3300 ml). The mixture was stirred at 25 to 30° C. for about 10 minutes. The layers were separated and aqueous layer was extracted with dichloromethane (325 ml.) and washed with water (1300 ml.). It was then dried over Na$_2$SO$_4$ and the solvent was distilled off on a water bath at a temperature in the range from 50 to 55° C. to obtain Clopidogrel free base (250 gms).

Clopidogrel base (250 gms) obtained above was dissolved in n-hexanol (1.25 L) with stirring at 25 to 30° C. Dilute sulfuric acid was added to it at 10 to 15° C. The reaction mixture was seeded with form-I crystal at 20 to 25° C. The mixture was stirred at room temperature, for 10-12 hrs and subsequently it was stirred at 22 to 25° C., for 1-2 hours at high agitation. The reaction mixture was further stirred for 5-8 hours at room temperature at low agitation. The mixture was then filtered, washed with methyl tert butyl ether (750 ml) and dried at 30 to 35° C. in a drier, to get 260 g of salt as crystals. Subsequent analysis confirmed that the crystals were clopidogrel hydrogen sulfate Form-I.

EXAMPLE 12

Preparation of Clopidogrel Hydrogen Sulfate Form I

A suspension of (S)-(+) Clopidogrel camphor sulphonate (861.3 gms) was stirred in dichloromethane (450 ml), and subsequently basified with NaHCO$_3$ solution (10%, 6500 ml). The mixture was stirred at 25 to 30° C. for about 10 minutes. The layers were separated and the aqueous layer was extracted with dichloromethane (900 ml.) and washed with water (1800 ml.). It was then dried over Na$_2$SO$_4$ and solvent was distilled off on a water bath at a temperature in the range from 50 to 55° C. to obtain Clopidogrel free base (500 gms).

Clopidogrel base (500 gms) obtained above was dissolved in n-hexanol (2.5 L) with stirring at 25 to 30° C. and water (10.3 ml) was added to it. Concentrated sulfuric acid was added to it at 10 to 15° C. The reaction mixture was seeded with form-I crystal at 20 to 25° C. The reaction mixture was stirred at room temperature for 10-12 hrs and subsequently it was stirred at 22 to 25° C., for 1-3 hours at high agitation. The reaction mixture was further stirred for 5-8 hours at room temperature at low agitation. Then, the reaction mixture was filtered, washed with methyl tert butyl ether (1500 ml) and dried at 30 to 35° C. in drier, to obtain 561 g of Clopidogrel bisulfate salt. Subsequent analysis confirmed that the crystals were clopidogrel hydrogen sulfate Form-I.

EXAMPLE 13

Preparation of Clopidogrel Hydrogen Sulfate Form I

A suspension of (S)-(+) Clopidogrel camphor sulphonate (430.65 gms) was stirred in dichloromethane (225 ml), and subsequently basified with NaHCO$_3$ solution (10%, 3250 ml). Stirred at 25 to 30° C. for about 10 minutes. The layers were separated and the aqueous layer was extracted with dichloromethane (450 ml.) and washed with water (900 ml.). It was then dried over Na$_2$SO$_4$ and distilled on a water bath at a temperature in the range from 50 to 55° C. to obtain Clopidogrel free base (250 gms).

Clopidogrel base (250 gms) was dissolved in n-hexanol (1.25 L) with stirring at 25 to 30° C. Dilute sulfuric acid was added at 10 to 15° C. The reaction mixture was seeded with form-I crystals at 20 to 25° C. The reaction mixture was stirred at room temperature, for 10-12 hrs and subsequently it was stirred at 22 to 25° C., for 1-3 hours at high agitation. The reaction mixture was further stirred for 5-8 hours at a room temperature at low agitation. It was then filtered, washed with methyl tert butyl ether (750 ml) and dried at 30 to 35° C. in a drier, to obtain 240 g of clopidogrel bisulfate salt. Subsequent analysis confirmed that the crystals were clopidogrel hydrogen sulfate Form-I.

EXAMPLE 14

Preparation of Clopidogrel Hydrogen Sulfate Form I

The amorphous form of Clopidogrel bisulfate (50 g) by any process mentioned above was dissolved in n-hexanol (250 mL) at 25 to 30° C. The reaction mixture was stirred for 12 hours. The precipitated solid was filtered, washed with methyl tert butyl ether (50 ml), and dried at 30 to 35° C. in a drier, to obtain 50 g of clopidogrel bisulfate salt. Subsequent analysis confirmed that the crystals were clopidogrel hydrogen sulfate Form-I.

EXAMPLE 15

Preparation of Clopidogrel Hydrogen Sulfate Form I

A suspension of Clopidogrel hydrogen sulfate (330 gms) was stirred in dichloromethane (1950 ml) and subsequently with NaHCO$_3$ solution (10%, 3300 ml). The mixture was stirred at 25 to 30° C. for about 10 minutes. The organic layer was separated and aqueous layer was extracted with dichloromethane (325 ml.) and washed with water (1300 ml.). It was then dried over Na$_2$SO$_4$ and the solvent was distilled off on a water bath at a temperature in the range from 50 to 55° C. to obtain Clopidogrel free base (250 gms).

Clopidogrel base (250 gms) was dissolved in n-hexanol (1.25 L) with stirring at 25 to 30° C. Dilute sulfuric acid was added to it at 10 to 15° C. The mixture was stirred at room temperature, for 6 hrs and subsequently it was stirred at 22 to 25° C., for 5 hours at high agitation. The reaction mixture was further stirred for 4-5 hours at room temperature at low agitation. The mixture was then filtered, washed with methyl tert butyl ether (750 ml) and dried at 30 to 35° C. in a drier, to get 280 g of salt as crystals. Subsequent analysis confirmed that the crystals were Clopidogrel hydrogen sulfate Form-I.

EXAMPLE 16

Preparation of Clopidogrel Hydrogen Sulfate Form I

A suspension of Clopidogrel hydrogen sulfate (330 gms) was stirred in dichloromethane (1950 ml) and subsequently basified with NaHCO$_3$ solution (10%, 3300 ml). The mixture was stirred at 25 to 30° C. for about 10 minutes. The layers were separated and the aqueous layer was extracted with dichloromethane (325 ml.) and washed with water (1300 ml.). It was then dried over Na$_2$SO$_4$ and distilled off on a water bath at a temperature in the range from 50 to 55° C. to obtain Clopidogrel free base (250 gms).

Clopidogrel base (250 gms) was dissolved in n-hexanol (1.25 L) with stirring at 25 to 30° C. and water (5 ml) was added to it. To the mixture was added concentrated sulfuric acid at 10 to 15° C. The mixture was stirred at room temperature for 6 hrs and subsequently it was stirred at 22 to 25° C., for 5 hours at high agitation. The reaction mixture was further stirred for 4 hours at room temperature at low agitation. The mixture was then filtered, washed with methyl tert butyl ether (750 ml) and dried at 30 to 35° C. in a drier, to get 270 g of Clopidogrel bisulfate salt as crystals. Subsequent analysis confirmed that the crystals were Clopidogrel hydrogen sulfate Form-I.

EXAMPLE 17

Preparation of Clopidogrel Hydrogen Sulfate Form I

A suspension of Clopidogrel camphor sulphonate (430.65 gms) was stirred in dichloromethane (225 ml), and subsequently basified with NaHCO$_3$ solution (10%, 3300 ml). The mixture was stirred at 25 to 30° C. for about 10 minutes. The layers were separated and the aqueous layer was extracted with dichloromethane (450 ml.) and washed with water (900 ml.). It was then dried over Na$_2$SO$_4$ and the solvent was distilled off on a water bath at a temperature in the range from 50 to 55° C. to obtain Clopidogrel free base (250 gms).

Clopidogrel base (250 gms) was dissolved in n-hexanol (1.25 L) with stirring at 25 to 30° C. Dilute sulfuric acid was added to it at 10 to 15° C. The mixture was stirred at room temperature for 6 hrs and subsequently it was stirred at 22 to 25° C., for 5 hours at high agitation. The reaction mixture was further stirred for 4 hours at room temperature at low agitation. The mixture was then filtered, washed with methyl tert butyl ether (750 ml) and dried at 30 to 35° C. in a drier to get 250 g of Clopidogrel bisulfate salt as crystals. Subsequent analysis confirmed that the crystals were Clopidogrel hydrogen sulfate Form-I.

EXAMPLE 18

Preparation of Clopidogrel Hydrogen Sulfate Form I

A suspension of Clopidogrel camphor sulphonate (430.65 gms) was stirred in dichloromethane (225 ml), and subsequently basified with NaHCO$_3$ solution (10%, 3300 ml). The reaction mixture was stirred at 25 to 30° C. for about 10 minutes. The layers were separated and the aqueous layer was extracted with dichloromethane (450 ml.) and washed with water (900 ml.). It was then dried over Na$_2$SO$_4$ and the solvent was distilled off on a water bath at a temperature in the range from 50 to 55° C. to obtain Clopidogrel free base (250 gms).

Clopidogrel base (250 gms) was dissolved in n-hexanol (1.25 L) with stirring at 25 to 30° C. and water (5 ml) was added followed by addition of concentrated sulfuric acid at 10 to 15° C. The mixture was stirred at room temperature, for 6 hrs and subsequently it was stirred at 22 to 25° C., for 5 hours at high agitation. The reaction mixture was further stirred for 4 hours at room temperature at low agitation. The mixture was then filtered, washed with methyl tert-butyl ether (750 ml) and dried at 30 to 35° C. in a drier, to get 280 g of Clopidogrel bisulfate salt as crystals. Subsequent analysis confirmed that the crystals were Clopidogrel hydrogen sulfate Form-I.

EXAMPLE 19

Preparation of Clopidogrel Hydrogen Sulfate Form I

Clopidogrel base (39 gms) was dissolved in n-heptanol (154 mL) with stirring at 25 to 30° C. and water (0.8 ml) was added to it. Concentrated H$_2$SO$_4$ was added at 10-15° C.°. The reaction mixture was seeded with form-I crystal at 20-25° C. The reaction mixture was stirred at room temperature, for 21 hrs. It was filtered, washed with methyl tert-butyl ether (50 ml) and dried at a temperature in the range from 30 to 35° C. in a drier, to get 42 g of salt as crystals. Subsequent analysis confirmed that the crystals were Clopidogrel hydrogen sulfate Form-I.

EXAMPLE 20

Preparation of Clopidogrel Hydrogen Sulfate Form I

Clopidogrel base (50 gms) was dissolved in n-heptanol (154 mL) with stirring at 25 to 30° C. and dilute H$_2$SO$_4$ was added at 10-15° C. The reaction mixture was seeded with form-I crystal at 20-25° C. The reaction mixture was stirred at room temperature, for 20-24 hrs, filtered, washed with methyl tert-butyl ether (50 ml) and dried at temperature in the range from 30 to 35° C. in a drier, to get 50 g of Clopidogrel bisulfate salt as crystals. Subsequent analysis confirmed that the crystals were Clopidogrel hydrogen sulfate Form-I.

EXAMPLE 21

Preparation of Clopidogrel Hydrogen Sulfate Form I

Clopidogrel base (10 gms) was dissolved in decan-1-ol (50 mL) with stirring at 25 to 30° C. and water (0.2 ml) was added to it. Concentrated H$_2$SO$_4$ was added at 10-15° C. Solid material precipitated. The mixture was stirred at room temperature, for 24 hrs. It was filtered, washed with methyl tert-butyl ether (30 ml) and dried at temperature in the range from 30 to 35° C. in a drier, to get 7 g of Clopidogrel bisulfate salt as crystals. Subsequent analysis confirmed that the crystals were clopidogrel hydrogen sulfate Form-I.

EXAMPLE 22

Preparation of Clopidogrel Hydrogen Sulfate Form I

Clopidogrel base (10 gms) was dissolved in decan-1-ol (50 mL) with stirring at 25 to 30° C. Dilute H$_2$SO$_4$ was added at 10-15° C. when the solid material precipitated. The reaction mixture was stirred at room temperature, for 24 hrs. Then the mixture was filtered, washed with methyl tert butyl ether (30 ml) and dried at a temperature in the range from 30 to 35° C. in a drier, to get 8 g of Clopidogrel bisulfate salt as crystals. Subsequent analysis confirmed that the crystals were of Clopidogrel hydrogen sulfate Form-I.

EXAMPLE 23

Preparation of Clopidogrel Hydrogen Sulfate Form I

The amorphous Clopidogrel bisulfate (50 g) was dissolved in methyl-tert-butyl ether (500 mL) at 25 to 30° C. The reaction mixture was stirred for 24 hours. Then the reaction mixture was filtered, washed with methyl tert-butyl ether (50 ml), and dried at 30 to 35° C. in a drier, to obtain 49 g of clopidogrel bisulfate salt Form-II. Subsequent analysis confirmed that the crystals were of Clopidogrel hydrogen sulfate Form-II.

We claim:

1. A process for preparing (S)-(+)-Clopidogrel bisulfate comprising:
    treating (S)-(+)-Clopidogrel base with dilute H$_2$SO$_4$ in a solvent selected from a member of the group consisting of hexanol, 2-hexanol, 3-hexanol, isohexanol, heptanol, 2-heptanol, 3-heptanol, 4-heptanol, octanol, iso-octanol, and decanol; and isolating (S)-(+)-Clopidogrel bisulfate from the solvent.

2. A process for preparing (S)-(+)-Clopidogrel bisulfate, comprising:
treating (S)-(+)-Clopidogrel base with concentrated $H_2SO_4$ in a solvent selected from a member of the group consisting of hexanol, 2-hexanol, 3-hexanol, isohexanol, heptanol, 2-heptanol, 3-heptanol, 4-heptanol, octanol, iso-octanol, decanol and water; and
isolating (S)-(+)-Clopidogrel bisulfate from the solvent.

3. A process for preparing (S)-(+)-Clopidogrel bisulfate, comprising:
dissolving or contacting (S)-(+)-Clopidogrel bisulfate in any form with a solvent selected from a member of the group consisting of hexanol, 2-hexanol, 3-hexanol, isohexanol, heptanol, 2-heptanol, 3-heptanol, 4-heptanol, octanol, iso-octanol, and decanol; and
isolating (S)-(+)-Clopidogrel bisulfate, from the solvent.

4. A process for preparing (S)-(+)-Clopidogrel bisulfate, comprising:
treating (S)-(+)-Clopidogrel bisulfate in any form with a solvent selected from a member of the group consisting of hexanol, 2-hexanol, 3-hexanol, isohexanol, heptanol, 2-heptanol, 3-heptanol, 4-heptanol, octanol, iso-octanol, and decanol and water; and
isolating (S)-(+)-Clopidogrel bisulfate from the solvent.

5. A process for preparing (S)-(+)-Clopidogrel bisulfate, comprising:
i. treating (S)-(+) Clopidogrel camphor-sulfonate in a mixture comprising a solvent and water with a base, to obtain (S)-(+)-Clopidogrel base, wherein the solvent is selected from a member of the group consisting of ethyl acetate, dichloromethane, dichloroethane, chloroform, and mixtures thereof;
ii. treating the (S)-(+)-Clopidogrel base with dilute $H_2SO_4$ in a solvent; and
iii. separating (S)-(+)-Clopidogrel bisulfate from the solvent.

6. A process for preparing (S)-(+)-Clopidogrel bisulfate, comprising:
i. treating (S)-(+) Clopidogrel camphor-sulfonate in a mixture comprising a solvent and water with a base, to obtain (S)-(+)-Clopidogrel base, wherein the solvent is selected from a member of the group consisting of ethyl acetate, dichloromethane, dichloroethane, chloroform, and mixtures thereof;
ii. treating the (S)-(+)-Clopidogrel base with concentrated $H_2SO_4$ in a mixture comprising a solvent and water; and
iii. separating (S)-(+)-Clopidogrel bisulfate from the solvent.

7. A process for preparing (S)-(+)-Clopidogrel bisulfate, comprising:
i. treating (S)-(+)-Clopidogrel base with dilute $H_2SO_4$ in a solvent, and
ii. separating (S)-(+)-Clopidogrel bisulfate from the solvent.

8. A process for preparing (S)-(+)-Clopidogrel bisulfate, comprising:
i. treating (S)-(+)-Clopidogrel base with concentrated $H_2SO_4$ in a solvent and water, and
ii. separating (S)-(+)-Clopidogrel bisulfate from the solvent.

9. A process for preparing (S)-(+)-Clopidogrel bisulfate, comprising:
i. treating (S)-(+)-Clopidogrel camphor-sulfonate in one or more solvent(s) with a base, to obtain (S)-(+)-Clopidogrel base, wherein the solvent is selected from a member the group consisting of ethyl acetate, dichloromethane, dichloroethane, chloroform, and mixtures thereof;
ii. treating the (S)-(+)-Clopidogrel base with dilute $H_2SO_4$ in a solvent(s); and
iii. separating (S)-(+)-Clopidogrel bisulfate from the solvent.

10. A process for preparing (S)-(+)-Clopidogrel bisulfate, comprising:
i. treating (S)-(+)-Clopidogrel camphor-sulfonate in a solvent with a base, to obtain (S)-(+)-Clopidogrel base, wherein the solvent is selected from a member of the group consisting of ethyl acetate, dichloromethane, dichloroethane, chloroform, and mixtures thereof;
ii. treating the (S)-(+)-Clopidogrel base with concentrated $H_2SO_4$ in a mixture comprising a solvent and water; and
iii. separating (S)-(+)-Clopidogrel bisulfate from the solvent.

11. The process of claim 1, wherein the base is selected from a member of the group consisting of NaOH, KOH, LiOH, $NaHCO_3$, $Na_2CO_3$, and $K_2CO_3$.

12. The process of claim 5, wherein step ii the solvent is selected from a member of the group consisting of hexanol, 2-hexanol, 3-hexanol, isohexanol, heptanol, 2-heptanol, 3-heptanol, 4-heptanol, octanol, iso-octanol, and decanol.

13. The process of claim 3, wherein the Clopidogrel bisulfate is in a form selected from a member of the group consisting of crystalline form, amorphous form and oil form.

14. The process of claim 4, wherein the Clopidogrel bisulfate is in a form selected from a member of the group consisting of crystalline form, amorphous form and oil form.

* * * * *